United States Patent [19]

Borodic

[11] Patent Number: 5,053,005
[45] Date of Patent: Oct. 1, 1991

[54] CHEMOMODULATION OF CURVATURE OF THE JUVENILE SPINE

[75] Inventor: Gary E. Borodic, 90 Kensington Dr., Canton, Mass. 02021

[73] Assignees: Gary E. Borodic, Canton; Edmund R. Pitcher, Hingham, both of Mass.

[21] Appl. No.: 341,538

[22] Filed: Apr. 21, 1989

[51] Int. Cl.$^5$ ............................................. A61M 31/00
[52] U.S. Cl. ...................................... 604/51; 128/898
[58] Field of Search ...................... 604/51, 49, 27, 28; 128/898

[56] References Cited

U.S. PATENT DOCUMENTS 4,932,936  6/1990  Dykstra et al. ....................... 604/51

OTHER PUBLICATIONS

Patrinely et al., 49 *Advances in Neurology*, 493-398 (1988).
Tagerud et al., 407 *Pflugers Archiv*, 275-278 (1986).
Duchen et al., 16-17 *Proc. Physiol. Soc.*, 2-4 (1966).
Pestronk et al., 199 *Science*, 1223-25 (1978).
Guyton et al., *Arch. Neur. Psychiat.*, 578-92 (1978).
Tonge, D. A., 241 *J. Physiol.*, 127-39 (1974).
Yee et al., 7 *J. Neurosci.*, 7:2019-24 (1987).
Pestronk et al., 264 *Nature*, 787-88 (1976).
Elston et al., 290 *Brit. Med. J.*, 181-83 (1985).
Dolly et al., 307 *Nature*, 457-60 (1984).
Simpson, Lance L., 229 *J. Pharmacol. Exp. Therapeutics*, 1:182-87 (1984).
Duchen, L. W., 33 *J. Neurol. Neurosurg. Psychiat.*, 40-54 (1970).
Drachman et al., 193 *Nature*, 1256-58 (1976).
Mauriello, Joseph A., M.D., 8 *Adv. Opthal. Plastic Reconstruct. Surgery*, 283-289 (1985).
Fiekers et al., 391 *J. Physiol.*, 109-124 (1987).
H. Gray, T. P. Pick, R. Howden, *Gray's Anatomy*, 337-350 (1901).
Figure A, unknown origin.

*Primary Examiner*—C. Fred Rosenbaum
*Assistant Examiner*—Mark O. Polutta
*Attorney, Agent, or Firm*—Testa, Hurwitz & Thibeault

[57] ABSTRACT

Disclosed is a non surgical method of modulating spinal curvature in developing vertebrates. Agents capable of temporarily interfering with neuromuscular transmission, e.g., botulinum toxin, are injected into the musculature of the back to create an imbalance in the muscular support of the developing spine. The procedure may be used to produced non human scoliosis animal models and in the clinical management of juvenile scoliosis.

7 Claims, 4 Drawing Sheets

CHEMOMODULATION OF CURVATURE OF THE JUVENILE SPINE

This invention relates to a non-surgical method of modulating spinal curvature in vertabrates during juvenile development. More specifically, the invention relates to inducing spinal curvature in experimental animals and decreasing the degree of spinal curvature in the developing axial skeleton of humans by non-surgical, temporary alteration of the balance of muscular support of the developing spine.

Scoliosis is a developmental curvature of the spine. Its cause has been attributed to congenital anomolies, neurogenic disease, extravertebral contractures, dystonias, and various idiopathic factors. The pathophysiology of scoliosis often involves a muscoskeletal tone imbalance which appears to result in a structural defect. It remains to be determined whether scoliosis skeletal changes cause the muscle imbalance or a preexisting muscle imbalance causes a developmental skeletal deformity.

Scoliosis appears in about 5% of all children and ranges in severity from barely preceptible skeletal anomolies to severe and sometimes life-threatening disfigurement. The adverse effects of mild scoliosis in children often can be alleviated by a regimen of exercise, use of corrective braces, traction, or nerve stimulation. In more severe cases, surgical intervention may be indicated. Surgery involves installation of a Harrington Rod through spinal vertebrae and a lengthy period in a body cast. The surgical option is warranted only when the degree of disfigurement outweighs the costs, potential psychological damage, patient discomfort, and surgical risks inherent to the procedure.

Experimentally, scoliosis has been induced in animal models by fusion of vertebrae, Rhizotomy, rib resection, operations on bone growth zones, and with radiation. Procedures for producing such animal models are of limited utility.

SUMMARY OF THE INVENTION

It has now been discovered that known toxic proteins which block muscle stimulation by, for example, inactivation of neuromuscular junctions, can be used titratably to alter the balance of muscular support of a developing juvenile spine thereby to influence spinal curvature. Experiments with laboratory animals have demonstrated that by altering muscle balance with sublethal doses of neurotoxins, a scoliotic spinal curvature can be induced and the degree of curvature can be controlled. Furthermore, the method can be used to reduce further curvature and to induce straightening of the scoliotic spine during the animal's development.

Accordingly, the invention provides a non-surgical method of modulating curvature of the spine during juvenile development of a vertebrate animal. The method comprises percutaneously injecting a neuromuscular blocking agent, for example, an acetylcholine transmission inhibitor, into the musculature of the back of the vertebrate at one or more sites disposed axially asymetrically of the spine. This results in alteration in the balance of muscular support of the developing spine. Various known drugs enable maintenance of this alteration of muscle balance with a single injection lasting from a few weeks to several months, and for longer periods using multiple injections. The procedure results in alteration in the curvature of the spine which persists after normal muscle function has returned.

In preferred aspects, the method of the invention comprises injecting an inhibitor of acetylcholine release such as a botulinum toxin or a protein which mimicks its acetylcholine release inhibiting effect. The currently preferred inhibitor is botulinum toxin A.

Accordingly, it is an object of the invention to provide methods of producing scoliotic animal models. Another object is to provide a non-surgical procedure for retarding the development of spinal curvature during juvenile development. These and other objects and features of the invention will be apparent from the following description, from the drawing, and from the appended claims.

DESCRIPTION

Figure 1:
FIG. 1 is an x-ray image showing a normal spine of a juvenile rabbit.

The invention is based on the discovery that spinal curvature can be modulated non-surgically by selectively and temporarily inactivating muscles or muscle groups responsible for spinal support. Practice of the invention involves the percutaneous injection of an agent capable of temporarily blocking muscle stimulation into one or more points in the musculature adjacent the spine of a developing vertebrate animal. The effect of the treatment is to alter the balance of muscular support for the developing spine thereby to alter the shape of the spine. Using the procedure disclosed herein, a spinal curvature of predetermined severity can be induced in an experimental animal in a predetermined direction or directions. Thus, the invention provides scoliotic animal models of various non-human species. Furthermore, the process enables non-surgical clinical treatment designed to alleviate scoliosis in appropriate cases of the condition in juvenile humans.

The currently preferred drugs for use in the procedure comprise proteinaceous neurotoxins secreted by various pathogenic bacteria known to interfere with neuromuscular transmission such as botulinum toxin. Several types of botulinum toxin are known. All are produced from *Clostridium botulinum*, and related anaerobic, gram positive pathogenic bacteria. Other toxins which potentially are useful include tetanus toxin, tetrodotoxin, and various animal venoms. Proteins produced using recombinant DNA technology which mimic the effects of these natural materials also may be used.

The currently preferred drug is botulinum A, a two-chain protein with an average molecular weight of about 140 to 150 thousand daltons. The material acts at the neuromuscular junctions to inhibit acetylcholine release from the presynaptic membranes and produces a dose-related weakness or paralysis of skeletal muscles. Botulinum acts by preventing exocytosis of acetylcholine into the synaptic gap. The heavy chain rapidly and irreversibly binds to the presynaptic membrane while the light chain interferes with exocytosis. While botulinum A is one of the most toxic substances per unit mass known, ($LD_{50}$ for humans is approximately 2 micrograms) it nevertheless has a very large therapeutic range and can be employed safely and effectively as evidenced, for example, by its established use in the treatment of neuromuscular disorders such as blepharospasms, hemifacial spasms (see e.g., Mauriello, Jr., Advanced Opthomalogical Plastic and Reconstructive Surgery, Vol. , pg. 283, 1985, and Elston et al, British Medical Journal, Vol. 290, pg. 181, 1985) and recent successes in the treatment of occupational and other dystonias (unpublished).

The preferred botulinum A toxin is available commercially from Dr. Allan Scott through the Smith-Kettlewell Eye Research Foundation of San Francisco, California under the trade name OCULINUM. One International Unit (IU) of the toxin is equal approximately to the $LD_{50}$ for a 20 gram mouse or, approximately $10^{-9}$ grams. The material is supplied in lyophilized form and is reconstituted by solution in saline.

Injection of small doses of the drug into the muscles induces an effect similar to denervation, resulting in loss of muscle tone or partial paralysis, depending on dosage, and subsequent muscle atrophy. Within two weeks to three months, motor nerve sprouting gradually restores normal muscle function. By the seventh to tenth day after injection, histological abnormalities in the pattern of motor nervation can be observed as thin nerve sprouts from terminal and preterminal motor nerve fibers appear. Up to the tenth week, the nerve sprouts over the atrophied muscle fibers become progressively more numerous and terminal arborizations are elongated.

Botulinum solution (12.5–100 IU/ml) may be administered by injection using, for example, a 25 gauge needle in a 1cc tuberculin syringe, directly into the paraspinal musculature, e.g., longissimus dorsi, erector spinae, spinalis, semispinalis, ilio-costalis, multifidus, intercostals, rhomboideus, trapezius, etc. Unlike denervation, the degree of blockage of muscle stimulation can be regulated by variation of dosage, variation in the sight of injection, and frequency of injection. The effects of the toxin generally last for a defined period of time within the range of three to six months, which varies among patients. Injections may be repeated if muscle tone and balance is to be maintained for longer periods.

The purpose of the injections is to alter intentionally the balance of muscular support of the spine temporarily, e.g., for a period of months, during which time a net stress is placed on the spine tending to induce a curvature or to correct a developing curvature, as desired. This is accomplished by weakening muscles with injections located axially asymmetrically about the spine so as to achieve the desired effect. Larger dosages produce greater muscle weakness and greater curvature. The site along the spine where the correction or induced curvature appears is dependent on the location(s) of the injection(s).

The effect of interfering with muscle inervation on one side of the back appears to produce a net stress on the developing spine. Thus, in a normal animal, administration of a muscle weakening drug on a given side of the musculature of the back causes a spinal curvature concave to the site or sites of injection. Similarly, in diagnosed scoliosis, developing spinal curvature can be alleviated, arrested, or reversed by interference with neuromuscular transmission in muscles adjacent the convex side of the curvature. Studies with primates will provide an experimental base permitting reproducible, conservative corrective procedures in various stages of scoliosis and degrees of severity.

Figure 2:
FIG. 2 is an x-ray image showing the development of a lateral spinal curvature in the rabbit of FIG. 1. On day 1, the rabbit was injected percutaneously with a total of 7.5 I.U. of bolulinum toxin A (BTA) at six sites into the paraspinal musculature (erector spinal) of the back on its right side. On day 15 the rabbit was reinjected with a total of 20 I.U. BTA at four points on the same side. On day 30 the rabbit was reinjected with at total of 20 I.U. BTA at three points on the same side. At day 36 the x-ray image of FIG. 2 was made. Note the beginning of a spinal curvature located in the region of the mid dorsal through mid lumbar spine which is with respect to the site of the site of the injections (rabbit's right side).
Figure 3:
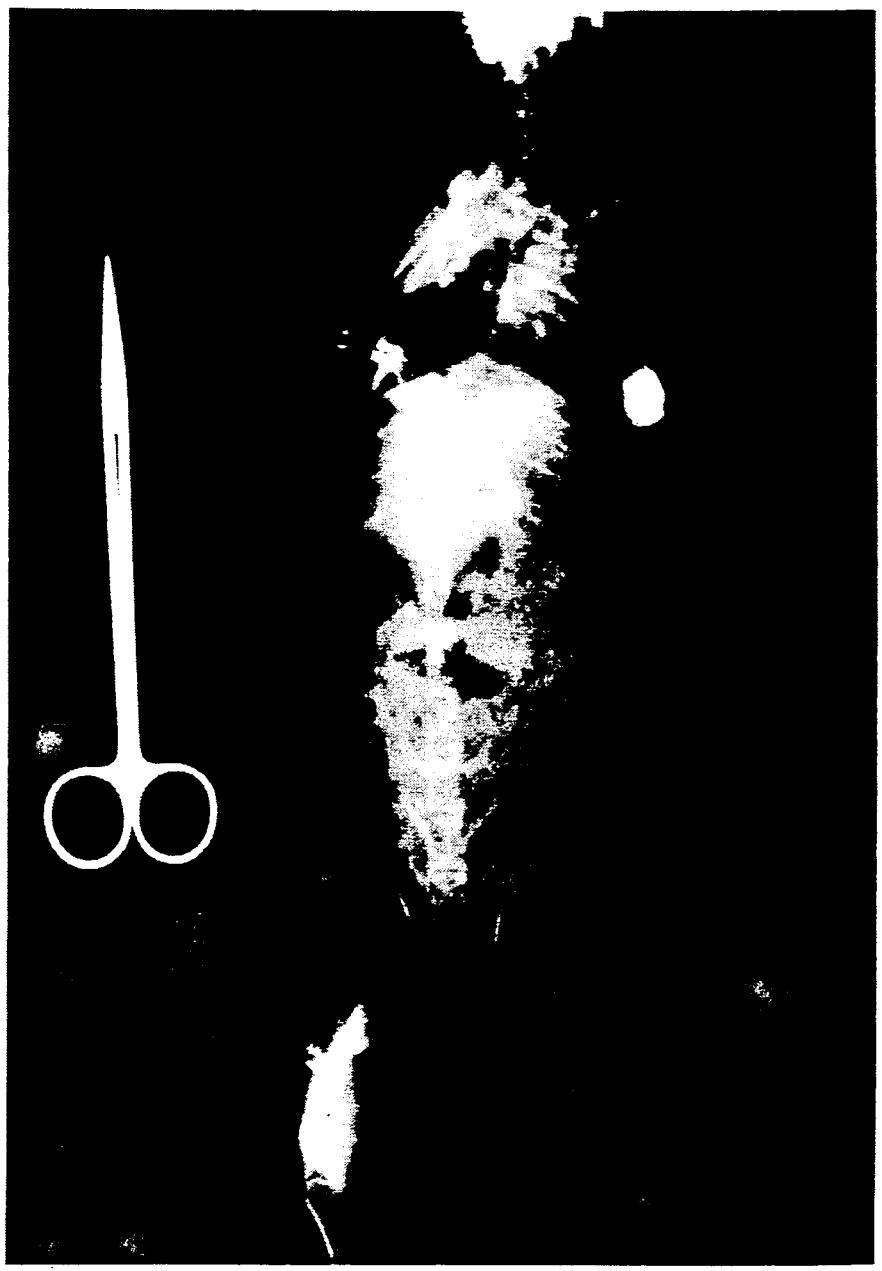
FIG. 3 is an x-ray image of the same rabbit taken at day 43. Note the increase, relative to FIG. 1, in lateral spinal curvature in the same region.
Figure 4:
FIG. 4 is an x-ray image of the same rabbit taken at day 91 showing an easily observed, permanent lateral spinal curvature.

FIGS. 1 through 4 illustrate the effects that can be achieved using the process of the invention. FIGS. 1 through 4 are x-ray images of a rabbit taken on day 1, 36, 43, and 91 (respectively) after initiation of treatment. The animal was a New Zealand white rabbit weighing 1.30 kilograms at the beginning of treatment and almost 3 kilograms at the time the x-ray of FIG. 4 was taken. The animal was treated by percutaneous injection, directly into the musculature of its right side using a 25 gauge needle, of 7.5 international units of OCULINUM (TM) dispersed about 6 points on day one, 20 international units of the drug at 4 points on day fifteen, and an additional 20 international units of the drug at 3 points on day thirty. As illustrated, a curvature is noticeable from the x-ray taken at day 36 (FIG. 2). At day 43, a more pronounced curvature has developed. At day 91 a pronounced, permananent lateral spinal curvature exists.

The dosage that would be used in a clinical procedure generally would not exceed 250–300 I.U. per injection point i.e., a dosage well above that employed in the treatment of blepherospasms and dystonias (10–150 I.U.) but far below the lethal dose for humans (about 0.03 microgram per kilogram). Experiments with botulinum A toxin in the treatment of human neurological disease at small doses has failed to elicit systemic side effects and produces only expected local effects related to temporary muscle atrophy.

The procedure of the invention would be applied clinically in those cases of scoliosis which are progressive and unresponsive to non-invasive forms of therapy such as exercises and back braces, e.g., a scoliosis patient who had been tried on exercise therapy and back braces but continued to have progressive angulation of the scoliotic curve. This type of patient would be a candidate for surgical intervention if the benefits of the surgical procedure outweighed the risks associated with corrective scoliosis surgery. The procedure as outlined herein would provide an alternative treatment modality.

Developmental scoliosis occurs during periods of rapid skeletal growth, and it is during these periods that the invention would be most appropriately applied. Clinically, once informed consent was obtained, angulation measurements of the axial skeleton would be made with conventional radiographics and computerized tonography. Once the location of the scoliotic curve was determined and the angulation quantitated, the erector spinae complex of the paraspinal muscles would be injected at 3 to 6 vertebral levels at a total dose range from 1.0 I.U./Kg body weight to 4.0 I.U./Kg body weight. The response to therapy would be determined by physical examination and radiographic analysis. Repeated injections at 6 to 12 week intervals would be anticipated in order to maintain a reduction of the paraspinal muscle tone and to augment the influence of muscle imbalance on spinal curvature. When beneficial response to treatment was obtained, (straightening of the bony spine), further use of the pharamacologic agent would be discontinued.

The invention may be embodied in other specific forms without departing from the spirit and scope thereof.

Other embodiments are within the following claims. What is claimed is:

1. A nonsurgical method of modulating curvature of the spine during juvenile development of a vertebrate animal, the method comprising the step of:

percutaneously injecting an acetylcholine transmission inhibitor, comprising an agent which mimics the effects of botulinum toxin to block muscle stimulation, into the musculature of the dorsal side of a vertebrate at a site disposed axially asymmetrically of the spine, thereby to produce alternation in the balance of muscular support of the developing spine lasting for a time sufficient to alter the curvature thereof.

2. The method of claim 1 wherein the inhibitor is a botulinum toxin.

3. The method of claim 1 wherein the inhibitor is botulinum toxin A.

4. The method of claim 1 wherein the vertebrate animal is a non-human mammal and said injecting step results in the development of an abnormal spinal curvature.

5. The method of claim 1 wherein the vertebrate animal has an abnormal spinal curvature and said inhibitor is injected at a position in said dorsal musculature to reduce further abnormal curvature during the animal's development.

6. A non surgical method of treating abnormal juvenile developmental spinal curvature in a mammal, the method comprising the step of:

percutaneously injecting an acetylcholine-release inhibitor derivative of a botulinum toxin into the musculature of the back of said mammal during its juvenile development at a site adjacent the spine to produce alteration of the balance of spinal muscular support in a direction favoring reduction of curvature and for a time sufficient to alter permanently the degree of spinal curvature.

7. The method of claim 6 wherein said inhibitor comprises botulinum A toxin.

* * * * *